United States Patent
Singh et al.

(10) Patent No.: US 10,446,875 B2
(45) Date of Patent: Oct. 15, 2019

(54) PHOSPHONIUM-BASED IONIC LIQUIDS FOR LITHIUM METAL-BASED BATTERIES

(71) Applicants: Toyota Motor Engineering & Manufacturing North America, Inc., Erlanger, KY (US); Deakin University, Geelong, Victoria (AU); Toyota Jidosha Kabushiki Kaisha, Toyota-Cho, Aichi-Ken (JP)

(72) Inventors: Nikhilendra Singh, Ypsilanti, MI (US); Timothy S. Arthur, Ann Arbor, MI (US); Kensuke Takechi, Ann Arbor, MI (US); Patrick Howlett, Box Hill South (AU); Maria Forsyth, Ashburton (AU); Robert Kerr, Croydon South (AU); Fuminori Mizuno, Miyoshi (JP)

(73) Assignees: Toyota Motor Engineering & Manufacturing North America, Inc., Plano, TX (US); Deakin University, Geelong, Victoria (AU)

( * ) Notice: Subject to any disclaimer, the term of this patent is extended or adjusted under 35 U.S.C. 154(b) by 133 days.

(21) Appl. No.: 15/606,964

(22) Filed: May 26, 2017

(65) Prior Publication Data
US 2018/0340000 A1 Nov. 29, 2018

(51) Int. Cl.
*H01M 10/0566* (2010.01)
*H01M 10/052* (2010.01)
(Continued)

(52) U.S. Cl.
CPC ....... *H01M 10/0566* (2013.01); *C07F 9/5407* (2013.01); *H01M 10/052* (2013.01); *H01M 10/0568* (2013.01); *H01M 2300/0045* (2013.01)

(58) Field of Classification Search
CPC ... H01M 10/0564–0569; H01M 10/052; C07F 9/5407
See application file for complete search history.

(56) References Cited

U.S. PATENT DOCUMENTS

| | | | |
|---|---|---|---|
| 6,053,953 A * | 4/2000 | Tomiyama ............ | H01M 4/382 29/623.1 |
| 2005/0136247 A1* | 6/2005 | Sumiya .................. | A01N 25/10 428/327 |

(Continued)

OTHER PUBLICATIONS

Girard et al., Electrochemical and physiochemical properties of small phosphonium cation ionic liquid electrolytes with high lithium salt content, Phys. Chem. Chem. Phys., 17, pp. 8706-9713 (2015).

(Continued)

*Primary Examiner* — Allison Bourke
(74) *Attorney, Agent, or Firm* — Christopher G. Darrow; Darrow Mustafa PC

(57) ABSTRACT

An electrolyte for Li-ion and other secondary electrochemical cells includes an FSI anion and at least one of methyltriethylphosphonium; trimethylisobutylphosphonium; methyltributylphosphonium; and trihexyltetradecylphosphonium. The electrolyte uniquely enables stable cell cycling even when water is present in the electrolyte at levels as high as 5000 ppm. Methyltriethylphosphonium and trimethylisobutylphosphonium-containing electrolytes are particularly effective in this water-stabilizing capacity.

20 Claims, 17 Drawing Sheets

(51) Int. Cl.
*H01M 10/0568* (2010.01)
*C07F 9/54* (2006.01)

(56) References Cited

U.S. PATENT DOCUMENTS

2014/0125292 A1* 5/2014 Best .................. H01M 10/0525
　　　　　　　　　　　　　　　　　　　　　　　　320/137
2018/0151916 A1* 5/2018 Howlett .................. H01G 11/62

OTHER PUBLICATIONS

Pozo-Gonzalo, C. et al., Redox Chemistry of the Superoxide Ion in a Phosphonium-Based Ionic Liquid in the Presence of Water, J. Phys. Chem. Lett., 2013, 4, pp. 1834-1837.
Pozo-Gonzalo, C. et al., Insights into the reversible oxygen reduction reaction in a series of phosphonium-based ionic liquids, Phys. Chem. Chem. Phys., 2014, 16, pp. 25062-25070.
Pozo-Gonzalo, C. et al., Enhanced performance of phosphonium based ionic liquids towards 4 electrons oxygen reductin reaction upon addition of a weak proton source, Electrochemistry Communications 38 (2014) pp. 24-27.
Mizuno, F. et al., Water in Ionic Liquid for Electrochemical Li Cycling, ACS Energy Lett., 1, pp. 542-547 (2016).

* cited by examiner

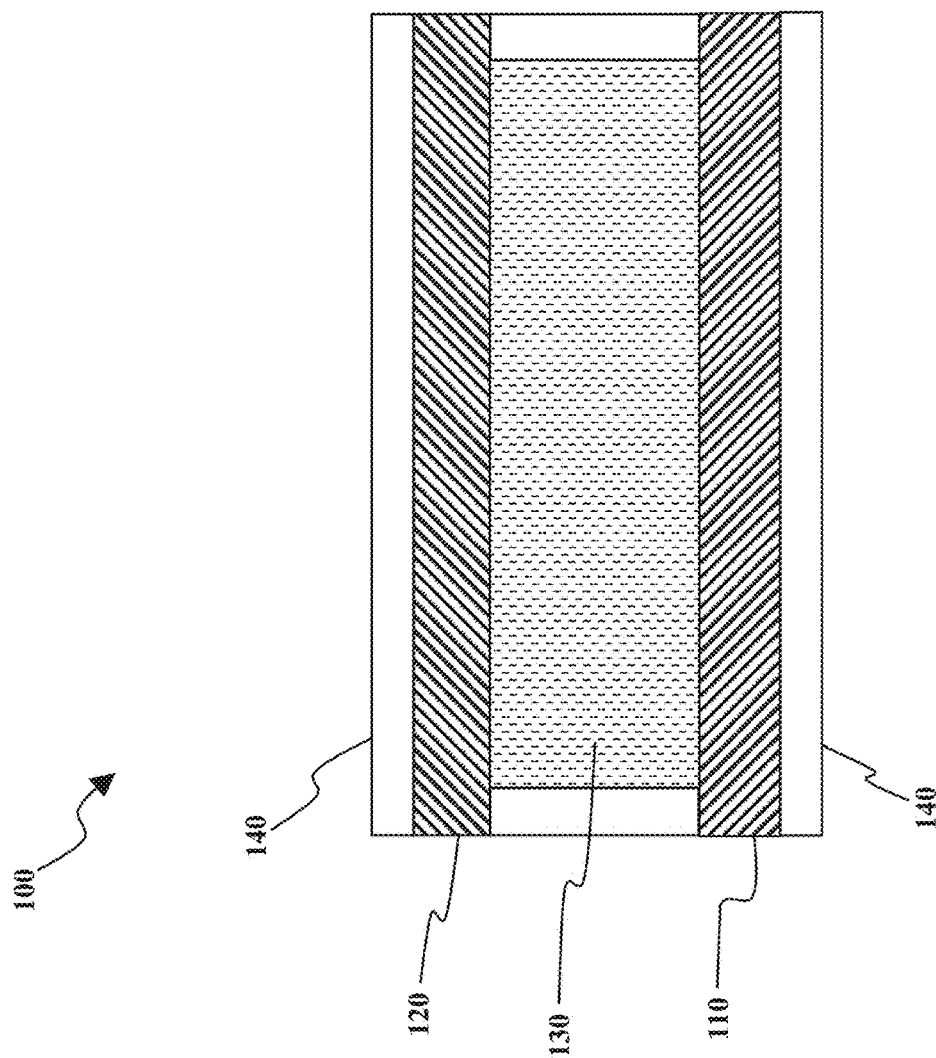

PHOSPHONIUM-BASED IONIC LIQUIDS FOR LITHIUM METAL-BASED BATTERIES

TECHNICAL FIELD

The present disclosure generally relates to water-tolerant electrolytes for Li-ion batteries and, more particularly, to such electrolytes containing phosphonium-based ionic liquids.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Ionic liquids are a class of electrolyte applicable to lithium metal-based battery technology. Ionic liquids, or "molten salts", are composed of ionic species, and most examples consist of a single/simple cation/anion pair. Their main attraction, in battery applications, include little-to-no vapor pressure below 100° C., unlimited combination of ions (like a designer solvent), wide and stable potential windows, non-flammable characteristics, ability to exclude water, high conductivities, and high solubility of metal salts. These attractions have led to ionic liquids being of great interest as compared to organic solvents.

Water reacts spontaneously with lithium metal, as well as other alkali and alkaline earth metals. Few, if any, ionic liquids or other electrolytes provide favorable lithium cycling results in the presence of water in the electrolyte. This is despite the well-known water exclusion capability of ionic liquids.

Accordingly, it would be desirable to provide an ionic liquid for a lithium electrolyte that permits stable electrochemical cycling capability while significant water is present in the electrolyte.

SUMMARY

This section provides a general summary of the disclosure, and is not a comprehensive disclosure of its full scope or all of its features.

In various aspects, the present teachings provide a Li-ion cell. The cell includes an anode, a cathode, and an electrolyte. The electrolyte has an active metal cation, configured to be reduced at the anode during charging; an organic cation; bis(fluorosulfonyl)imide anion; and water present at a concentration of at least 50 ppm. The organic cation is selected from the group consisting of: methyltriethylphosphonium; trimethylisobutylphosphonium; methyltributylphosphonium; and trihexyltetradecylphosphonium.

In other aspects, the present teachings provide an electrolyte. The electrolyte has an active metal cation, configured to be reduced at the anode during charging; an organic cation; bis(fluorosulfonyl)imide anion; and water present at a concentration of at least 50 ppm. The organic cation is selected from the group consisting of: methyltriethylphosphonium; trimethylisobutylphosphonium; methyltributylphosphonium; and trihexyltetradecylphosphonium.

Further areas of applicability and various methods of enhancing the above coupling technology will become apparent from the description provided herein. The description and specific examples in this summary are intended for purposes of illustration only and are not intended to limit the scope of the present disclosure.

BRIEF DESCRIPTION OF THE DRAWINGS

The present teachings will become more fully understood from the detailed description and the accompanying drawings, wherein:

FIG. 1 is a schematic illustration of a secondary electrochemical cell of the present disclosure;

Figure 2C:
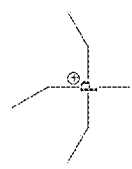
FIGS. 2A-2D are line drawings of the phosphonium cations of the present disclosure.

It should be noted that the figures set forth herein are intended to exemplify the general characteristics of the methods, algorithms, and devices among those of the present technology, for the purpose of the description of certain aspects. These figures may not precisely reflect the characteristics of any given aspect, and are not necessarily intended to define or limit specific embodiments within the scope of this technology. Further, certain aspects may incorporate features from a combination of figures.

DETAILED DESCRIPTION

The present teachings provide ionic liquids as electrolyte components for Li-metal based battery systems that possess favorable electrochemical properties and that enable high tolerance for water in the electrolyte composition. The disclosed ionic liquids demonstrate high salt solubility, excellent ionic conductivity, and strong stability toward anodic reduction. Further, the present teachings show that the disclosed ionic liquids possess an unusually strong ability to facilitate multiple electrochemical cycling in the presence of water, without substantial overpotential increases and failure that would typically attend the presence of water.

The ionic liquids of the present disclosure include one of four disclosed phosphonium cations and bis(fluorosulfonyl) imide. When employed as the solvent in an electrolyte composition, they can provide dramatic stabilization to a battery anode against water.

FIG. 1 illustrates a secondary electrochemical cell 100. The cell 100 of the present disclosure can include an anode 110, a cathode 120, and an electrolyte 130 in contact with the anode 110. It will be understood that the term "anode", as used herein, refers to an electrode at which electrochemical oxidation occurs during discharge of the cell 100 and at which electrochemical reduction occurs during charging of the cell 100. Similarly, the term "cathode", as used herein, refers to an electrode at which electrochemical reduction occurs during discharge of the cell 100 and at which electrochemical oxidation occurs during charging of the cell 100.

In various implementations, the cell 100 will be a Li-ion cell. In many such implementations, the anode 110 will be lithium metal, but can also include other suitable anode materials such as, without limitation, $Li_4Ti_5O_{12}$, $Mo_6S_8$, $Cu_2V_2O_7$, $TiS_4$, $NbS_5$, Li terephthalate ($C_8H_4Li_2O_4$), silicon, sulfur, graphite, nickel, and mixtures thereof. The cathode 120 can include any kind of cathode active material that is compatible with Li-ion cell electrochemistry. Suitable examples of cathode materials can include, without limitation, $LiMn_2O_4$, $LiCoO_2$, $LiFe(PO_4)$, $LiMn_{1/3}Ni_{1/3}Co_{1/3}O_2$, $LiNi_{0.5}Mn_{1.5}O_4$, $LiCoPO_4$, platinum, and mixtures thereof.

In other implementations, the cell 100 can be a sodium cell, a magnesium cell, or another secondary electrochemical cell. In such implementations, the anode 110 can be formed of the active metal, or another suitable anode material, and the cathode 130 can be formed of a compatible cathode material.

Figure 2D:
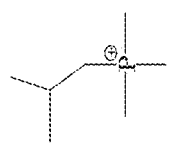
Figure 2B:
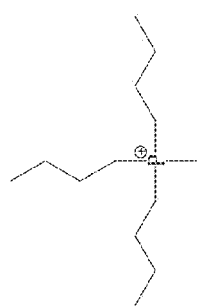
Figure 2A:
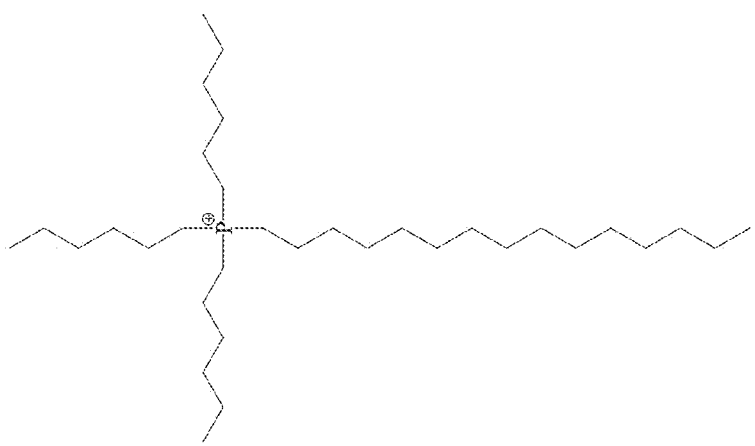

The electrolyte 130 includes a salt of an active metal cation and bis(fluorosulfonyl)imide (FSI), the active metal cation configured to be reduced at the anode during charging of the cell 100. For example, in the case of a Li-ion battery, the electrolyte includes LiFSI. The electrolyte further includes an ionic liquid having an FSI anion and at least one phosphonium cation from the group including: trihexyltetradecylphosphonium ($P_{6,6,6,14}$; FIG. 2A), methyltributylphosphonium ($P_{1,4,4,4}$; FIG. 2B), methyltriethylphosphonium ($P_{1,2,2,2}$; FIG. 2C), and trimethylisobutylphosphonium ($P_{1,1,1,i4}$; FIG. 2D). In some implementations, the salt will be present, relative to the ionic liquid, at a molar ratio of at least 1:5; or at least 1:2; or at least 1:1. In some implementations, the salt will be present at its saturation point in the ionic liquid (i.e. the electrolyte 130 is a saturated solution of salt in ionic liquid).

In various implementations, the electrolyte 130 can include water present in an amount of: at least 50 ppm; or at least 100 ppm; or at least 200 ppm; or at least 300 ppm; or at least 400 ppm; or at least 500 ppm; or at least 600 ppm; or at least 700 ppm; or at least 800 ppm; or at least 900 ppm; or at least 1000 ppm; or at least 2000 ppm; or at least 3000 ppm; or at least 4000 ppm. In some implementations, the electrolyte 130 can include water at any of the aforementioned minima, and with a maximum of 5000 ppm. In some implementations, the electrolyte 130 can include water present within a range of 5000-10000 ppm, inclusive. An electrolyte 130 having less than 50 ppm water will be referred to herein as "dry." Water content as discussed herein can be determined by the Karl Fischer titration.

Figure 3:
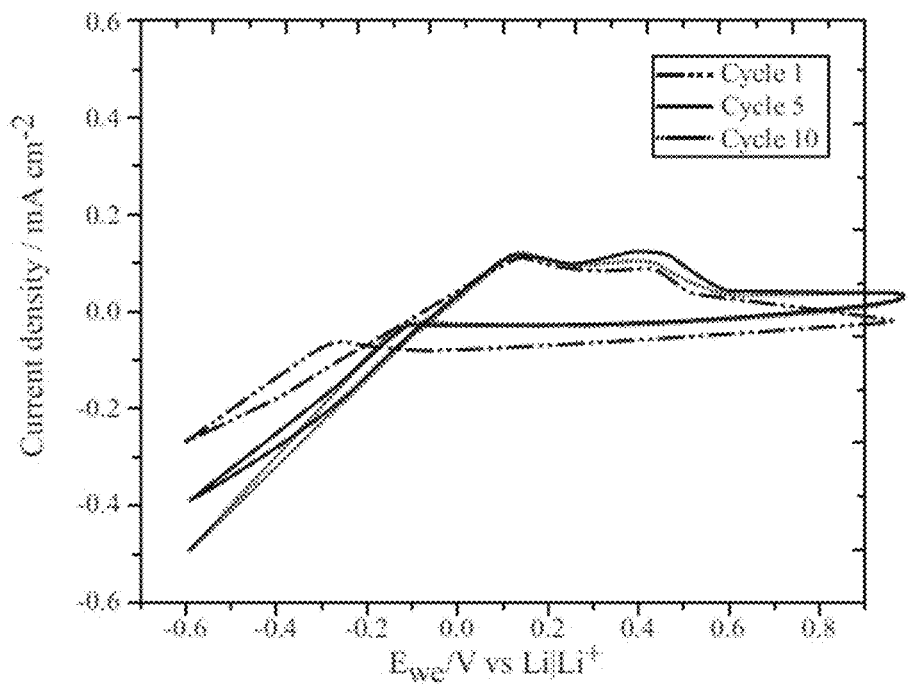
FIG. 3 is a cyclic voltammogram of a cell having an electrolyte with $[P_{6,6,6,14}][FSI]$ ionic liquid.

FIG. 3 shows a cyclic voltammetry plot of current density vs electric potential on a nickel working electrode and an electrolyte having 0.75 mol/kg LiFSI and an ionic liquid of $[P_{6,6,6,14}][FSI]$, with a $Li^+:P^{3+}$ mole ratio of 1:2. The results confirm that the disclosed ionic liquid supports reversible lithium deposition/stripping, albeit at relatively low rate in the case of $[P_{6,6,6,14}][FSI]$.

Figure 4A:
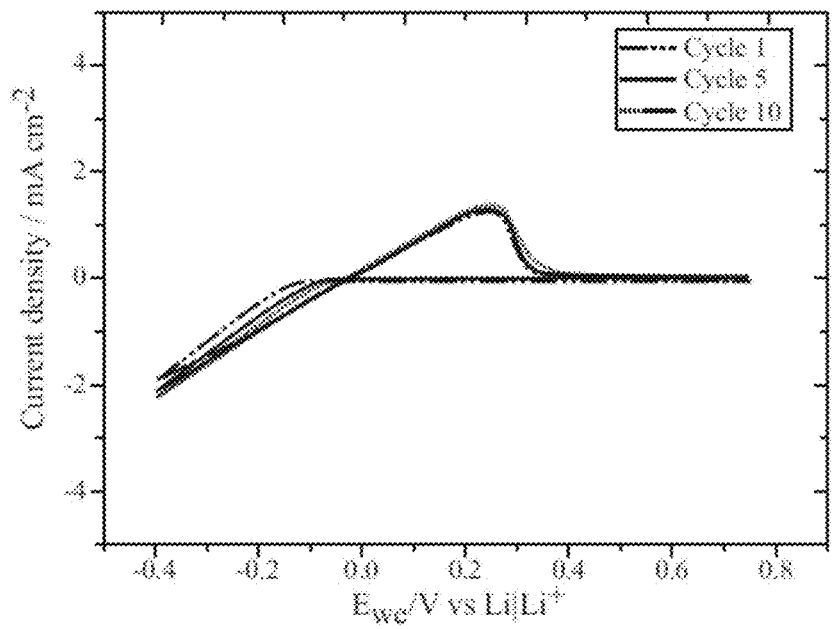
FIGS. 4A-4C are cyclic voltammograms of cells having electrolyte with $[P_{1,4,4,4}][FSI]$ ionic liquid and $Li^+:P^+$ molar ratios of 1:1, 1:2, and 1:5, respectively.
Figure 4B:
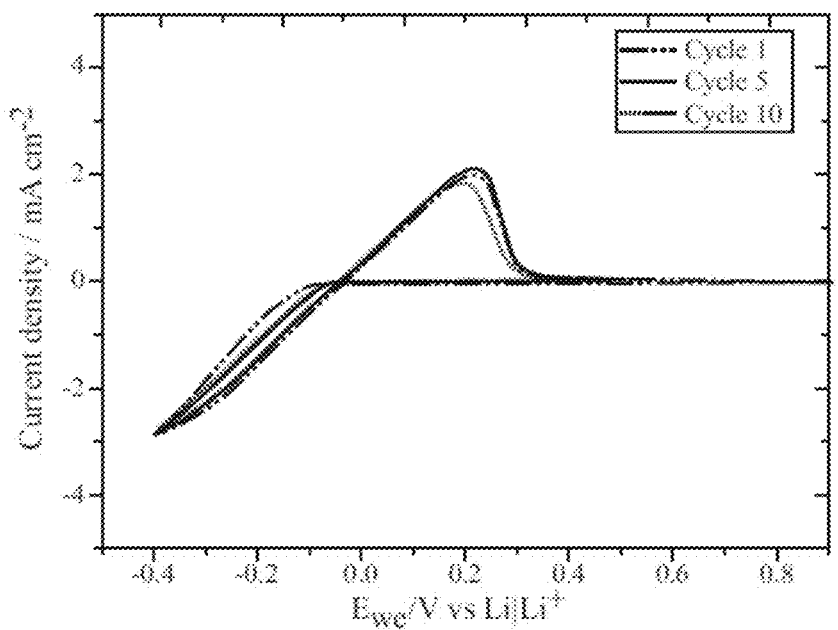
Figure 4C:
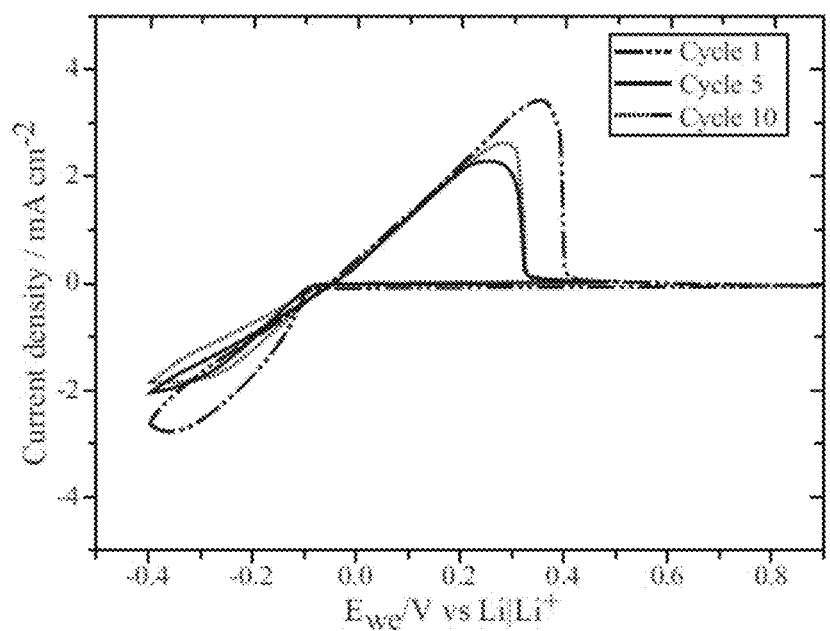
Figure 5A:
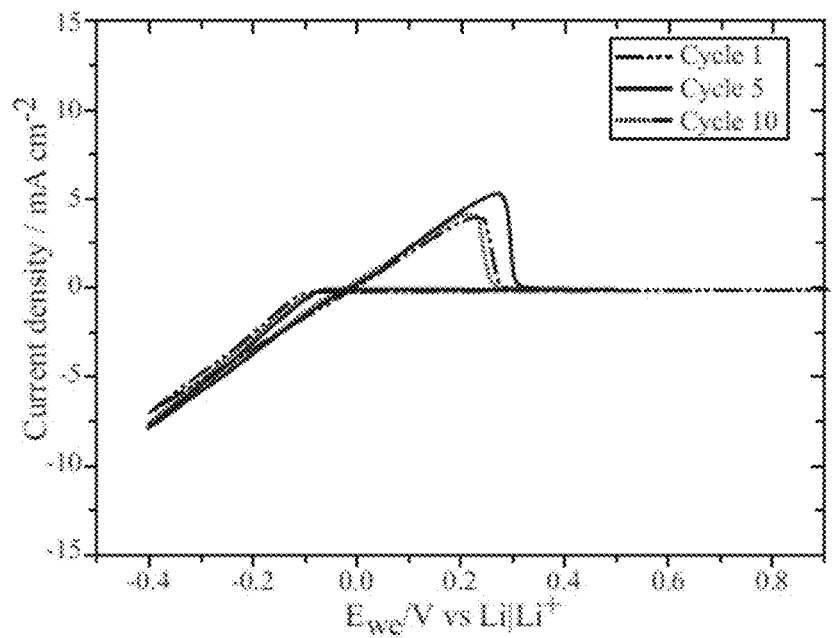
FIGS. 5A-5C are cyclic voltammograms of cells having electrolyte with $[P_{1,2,2,2}][FSI]$ ionic liquid and $Li^+:P^+$ molar ratios of 1:1, 1:2, and 1:5, respectively.
Figure 5B:
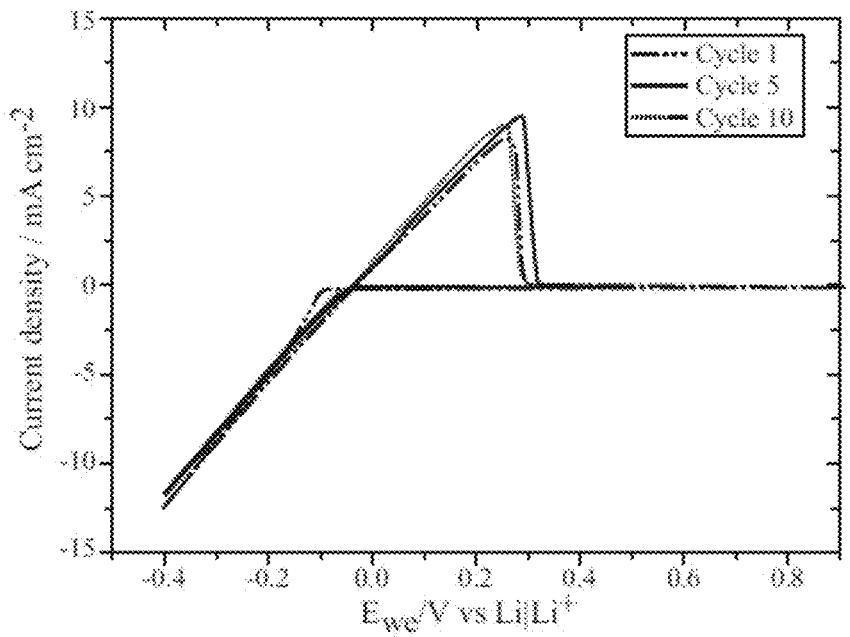
Figure 5C:
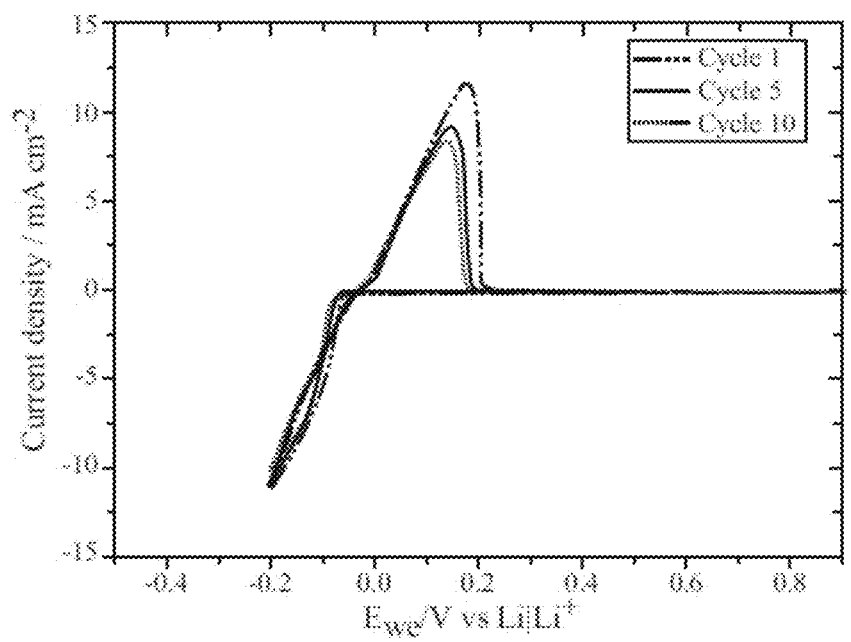

FIGS. 4A-4C show analogous results with $[P_{1,4,4,4}][FSI]$, and with LiFSI present at about 2.5, 1.25, and 0.5 mol/kg, respectively ($Li^+:P^{3+}$ mole ratio are 1:1, 1:2, and 1:5, respectively). The results show that $[P^{1,4,4,4}][FSI]$ supports reversible lithium deposition/stripping across a similar electrochemical window but at a much higher rate. Further, rate increases with decreasing LiFSI concentration. FIGS. 5A-5C show analogous results with $[P_{1,2,2,2}][FSI]$, and with LiFSI present at about 3.2, 1.6, and 0.65 mol/kg, respectively ($Li^+:P^+$ mole ratio are, again, 1:1, 1:2, and 1:5, respectively). The results show that $[P_{1,2,2,2}][FSI]$ supports yet higher deposition/stripping rates, and that rate once again increases with decreasing LiFSI concentration. Without being bound to any theory, it is believed that increased current density obtained with smaller phosphonium cations and with lower LiFSI concentration is likely attributable, at least in part, to viscosity effects.

Figure 6A:
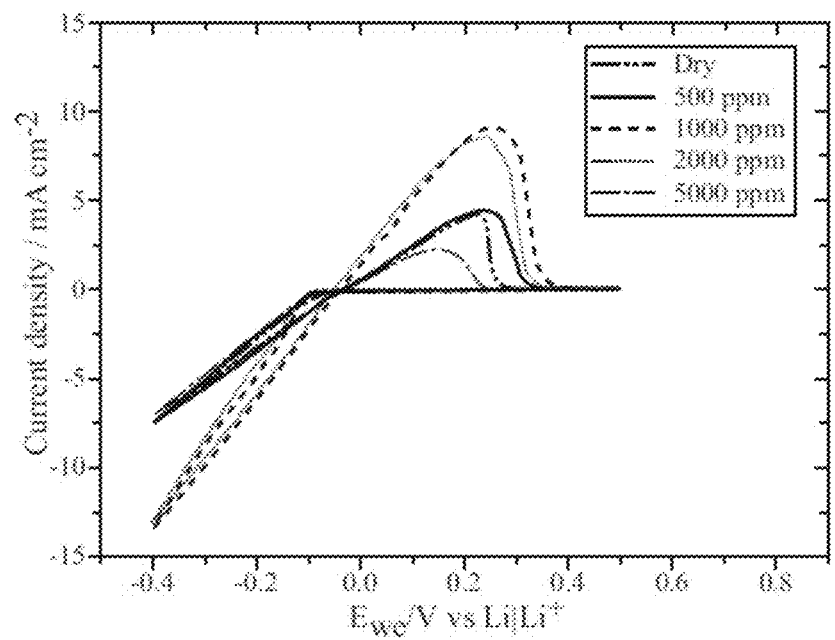
FIGS. 6A and 6B are cyclic voltammograms of the cells of FIGS. 5A and 5B, but with the addition of varying amounts of water to the electrolyte.
Figure 6B:
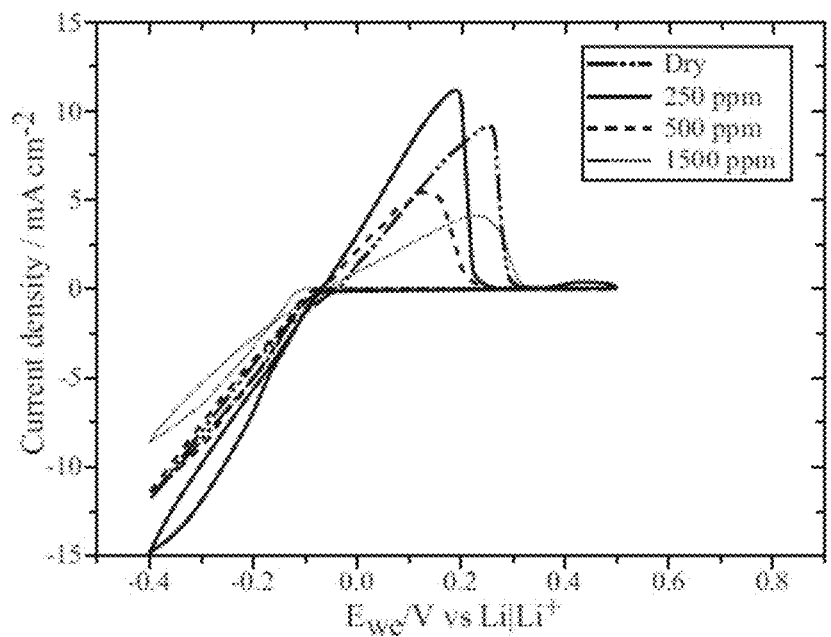
Figure 7A:
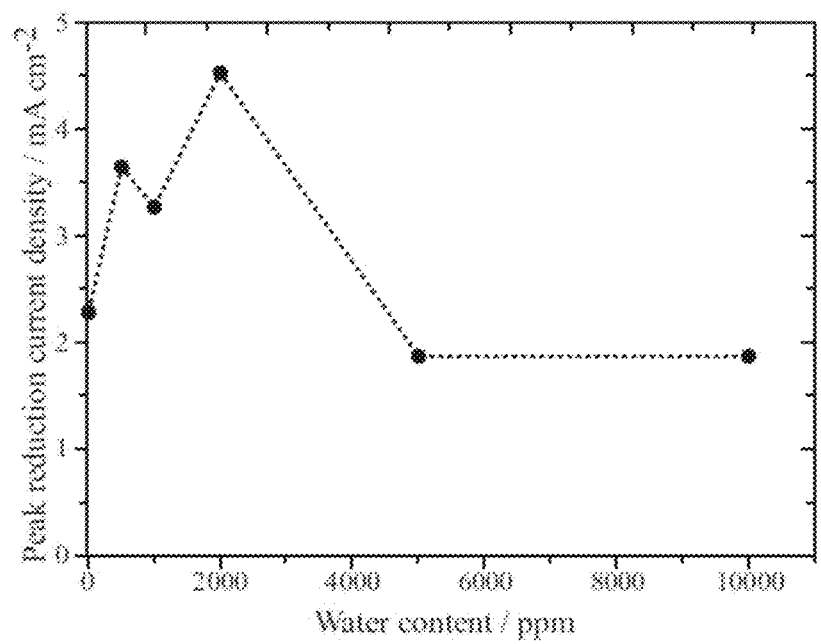
FIGS. 7A-7D are plots of maximum current density of lithium deposition as a function of water content for the cells of FIGS. 4A, 4B, 5A, and 5B, respectively.
Figure 7B:
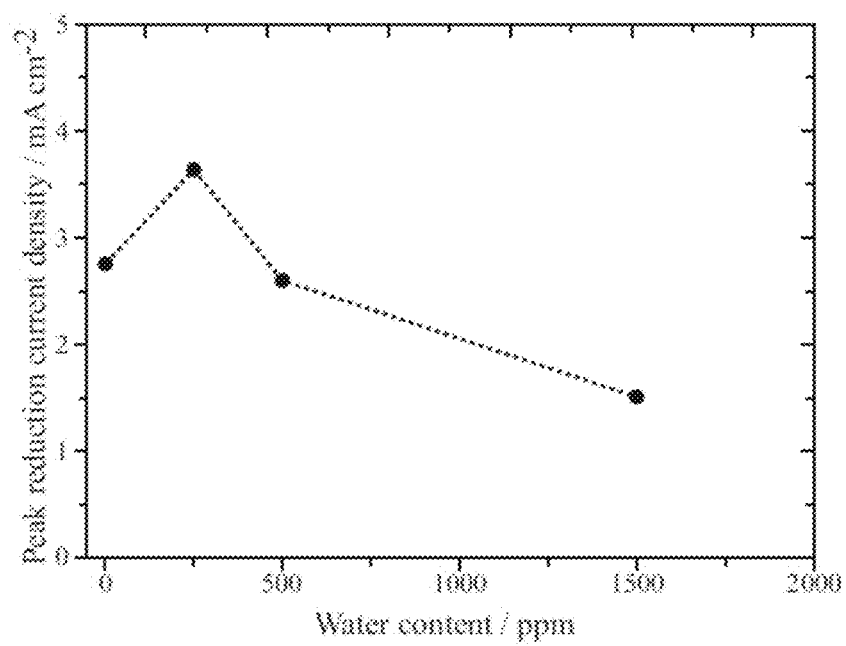
Figure 7C:
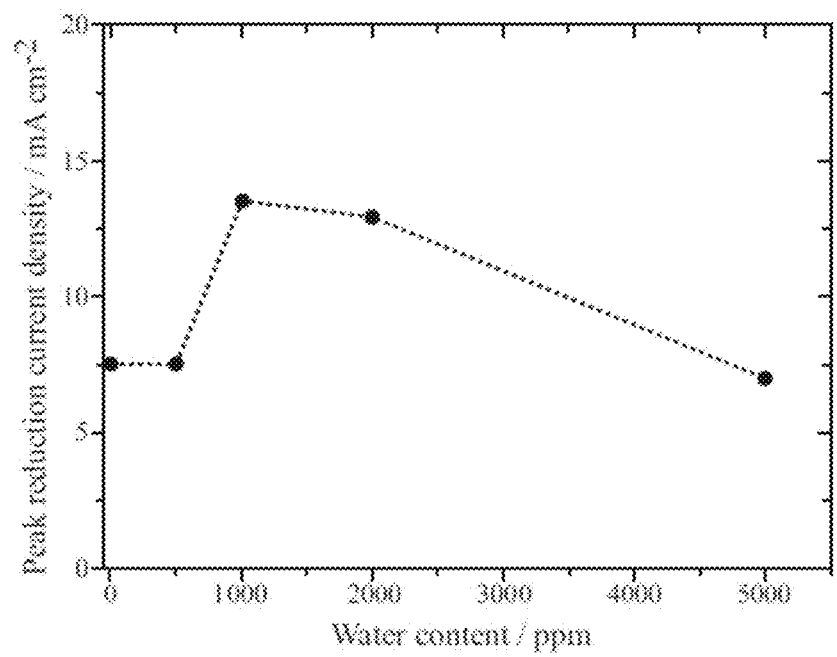
Figure 7D:
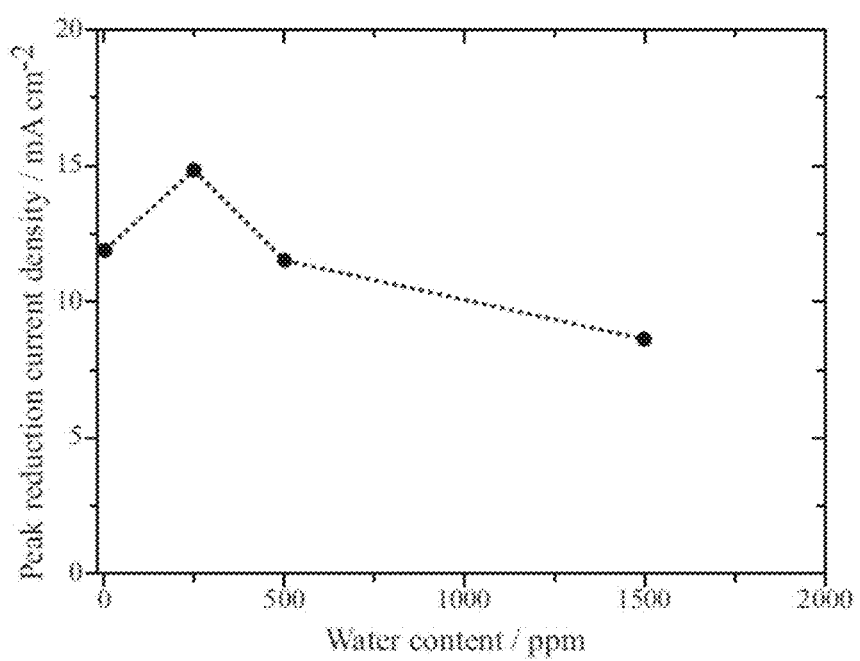

FIGS. 6A and 6B illustrate cyclic voltammograms of the cells of FIGS. 5A and 5B, but with the addition of varying amounts of water to the electrolyte, as indicated in the respective legends. The results show that the electrolyte continues to support reversible lithium deposition/stripping in the presence of water. Surprisingly, the results further indicate that the addition of some water increases the rate of lithium deposition, with an intermediate water content providing maximum deposition rate. Further, decreased LiFSI concentration decreases the water concentration that provides maximum deposition rate.

This effect is summarized in FIGS. 7A-7D, showing plots of peak reduction (deposition) current density as a function of water content for 3-electrode cells having 1:1 $Li^+:P_{1,4,4,4}$; 1:2 $Li^+:P_{1,4,4,4}$; 1:1 $Li^+:P_{1,2,2,2}$; and 1:2 $Li^+:P_{1,2,2,2}$; respectively.

Figure 8A:
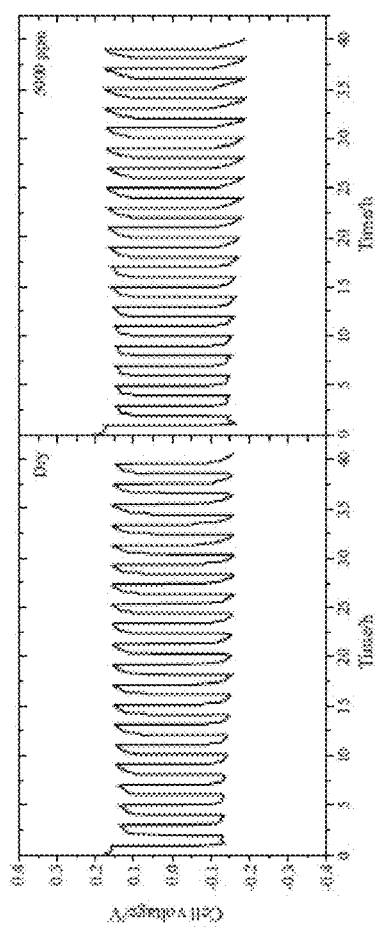
FIGS. 8A-8C are plots of cell voltage vs. time for symmetric cells having $[P_{1,4,4,4}][FSI]$ ionic liquid in the absence or presence of 5000 ppm water, at 1:1, 1:2, and 1:5 molar ratios of $Li^+:P^+$, respectively.
Figure 8B:
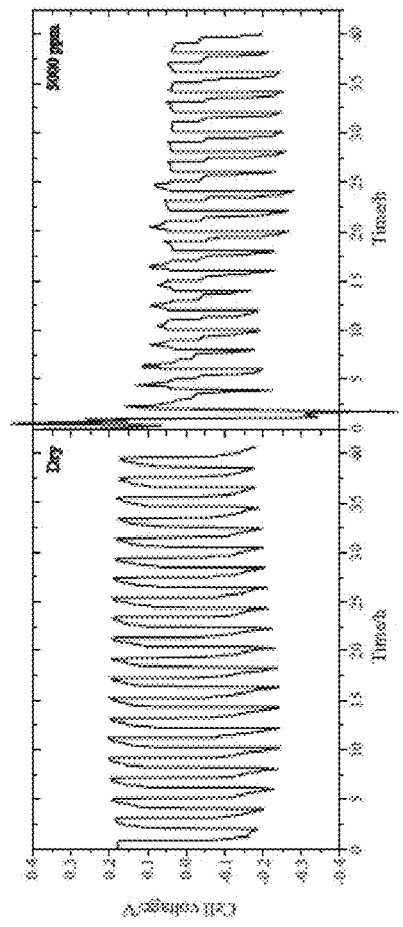
Figure 8C:
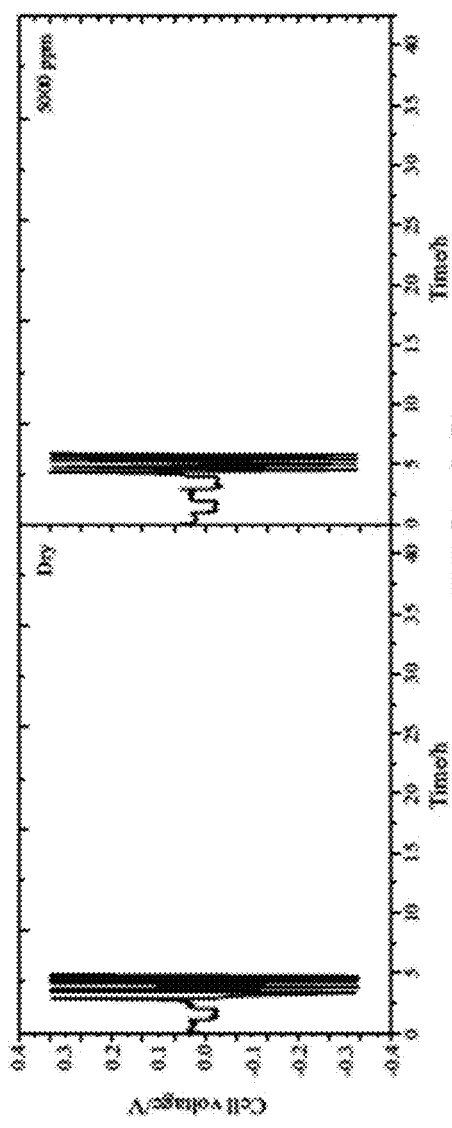
Figure 9A:
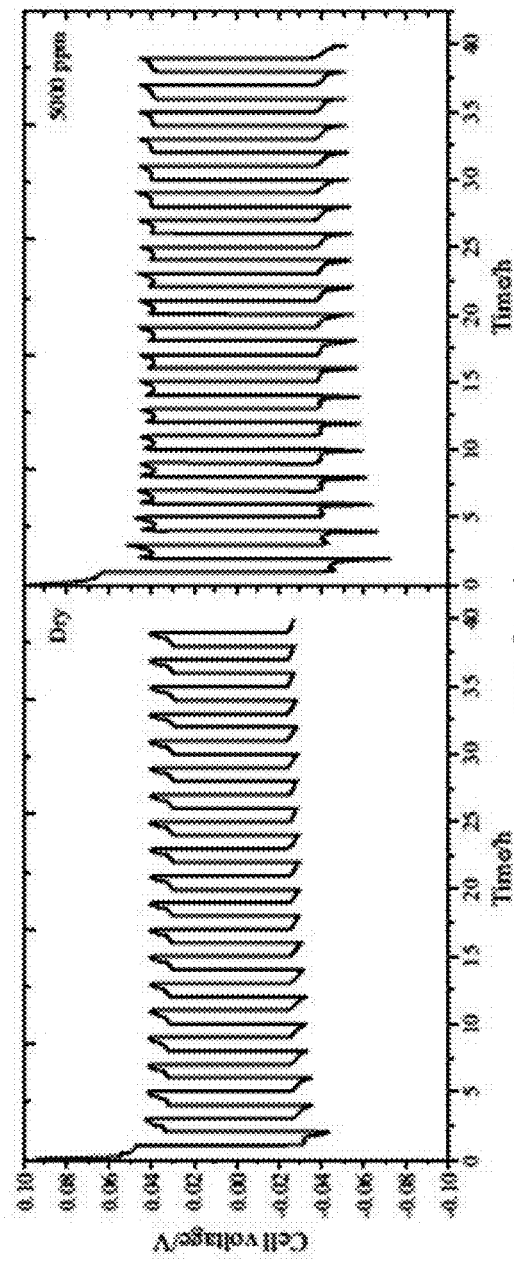
FIGS. 9A-9C are plots of cell voltage vs. time for symmetric cells having $[P_{1,2,2,2}][FSI]$ ionic liquid in the absence or presence of 5000 ppm water, at 1:1, 1:2, and 1:5 molar ratios of $Li^+:P^+$, respectively.
Figure 9B:
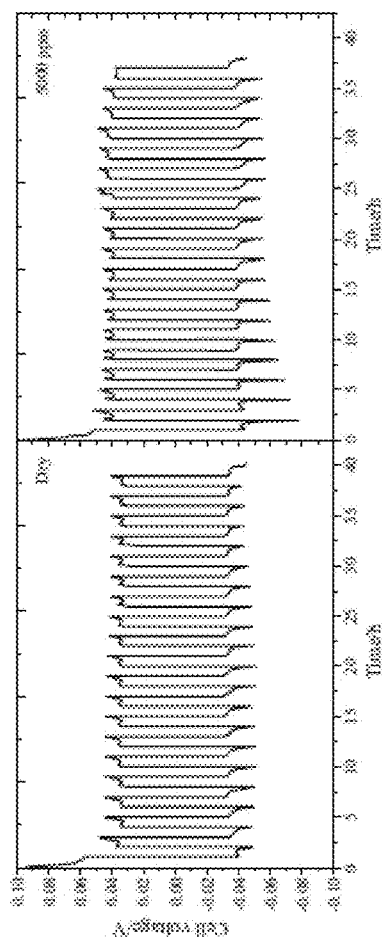
Figure 9C:
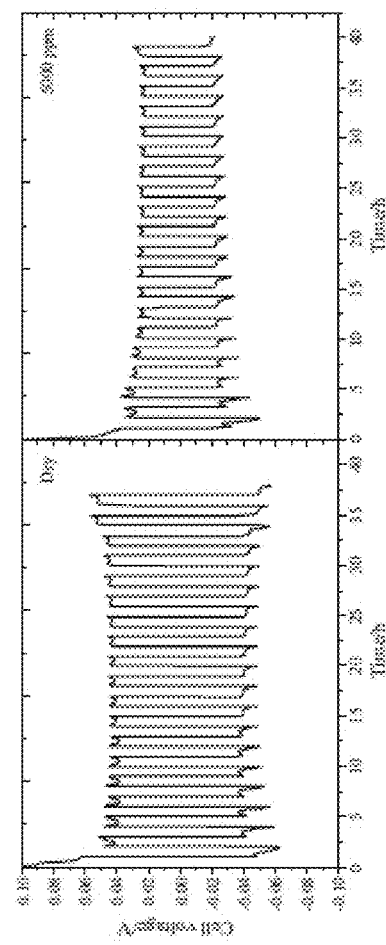

FIGS. 8A-8C illustrate cycling data for symmetric cells having $P_{1,4,4,4}$:FSI ionic liquid in the absence or presence of 5000 ppm water, at 1:1, 1:2, and 1:5 molar ratios of $Li^+:P^+$, respectively. The high lithium cell (FIG. 8A) shows stable cycling in the absence or presence of water during the entire cycling duration. The intermediate lithium concentration cell (FIG. 8B) shows erratic cycling in the presence of 5000 ppm water, and the low lithium concentration cell (FIG. 8C) does not cycle successfully. The analogous data for cells having $P_{1,2,2,2}$:FSI ionic liquid (FIGS. 9A-9C) show stable cycling in the absence or presence of water at all LiFSI concentrations, The addition of 5000 ppm water results in a slight increase to the cell voltages of approximately 15 mV in the case of 1:1 and 1:2 $Li^+:P^+$. Surprisingly, cell voltages are lowered by approximately 20 mV when water is introduced to the lowest lithium concentration cell (FIG. 9C). As used herein, the phrase "stable cycling" can, in some implementations, refer to a cell exhibiting an overpotential of less than ±1 V after 100 cycles. In some implementations, the phrase "stable cycling" can refer to a cell exhibiting an overpotential of less than ±0.5 V; or less than ±0.3 V; or less than ±0.2 V; after 100 cycles.

Figure 10:
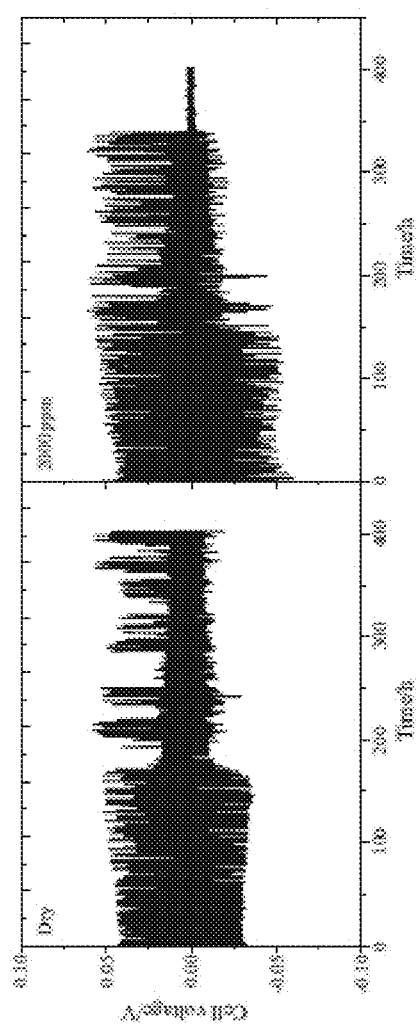
FIG. 10 is a pair of long duration plots of cell voltage vs. time for symmetric cells having $P_{1,2,2,2}$:FSI ionic liquid with 1:1 $Li^+:P^+$ in the absence of presence of 2000 ppm water.

FIG. 10 shows plots of extended cycling measurements performed on cells having $P_{1,2,2,2}$:FSI ionic liquid with 1:1 $Li^+$:$P^+$ in the absence or presence of 2000 ppm water. The voltage profile shows that for both cells, the electrode polarization remains constant at around 50 mV for 150 hours. After this point, both cells exhibit erratic behavior, leading to lower overpotentials.

Figure 11A:
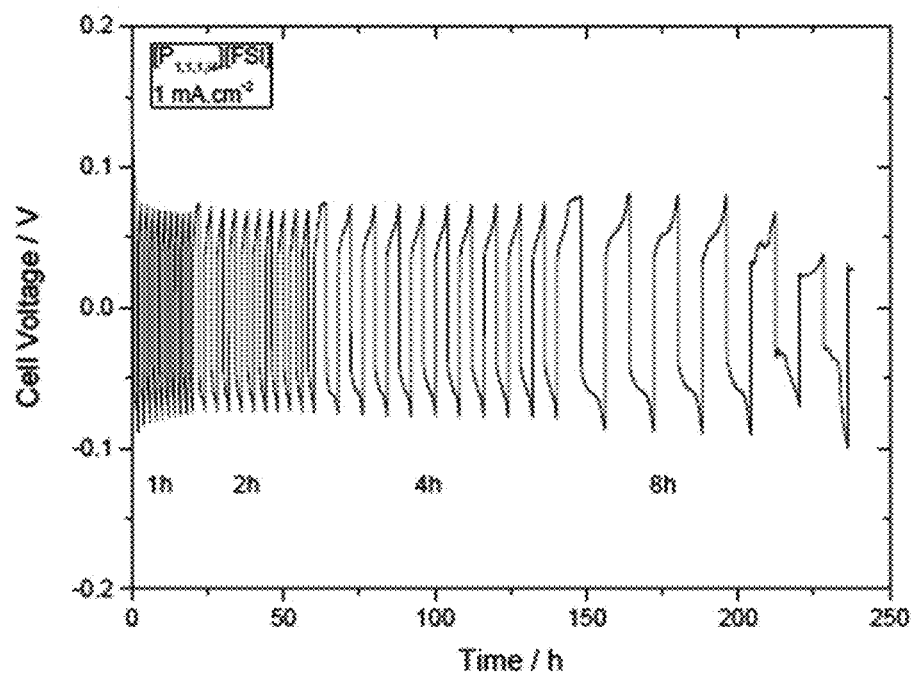
FIGS. 11A and 11B are plots of cell voltage vs. time for symmetric cells having ionic liquid or $P_{1,2,2,2}$:FSI ionic liquid, respectively, having increasing step times while holding current density constant.
Figure 11B:
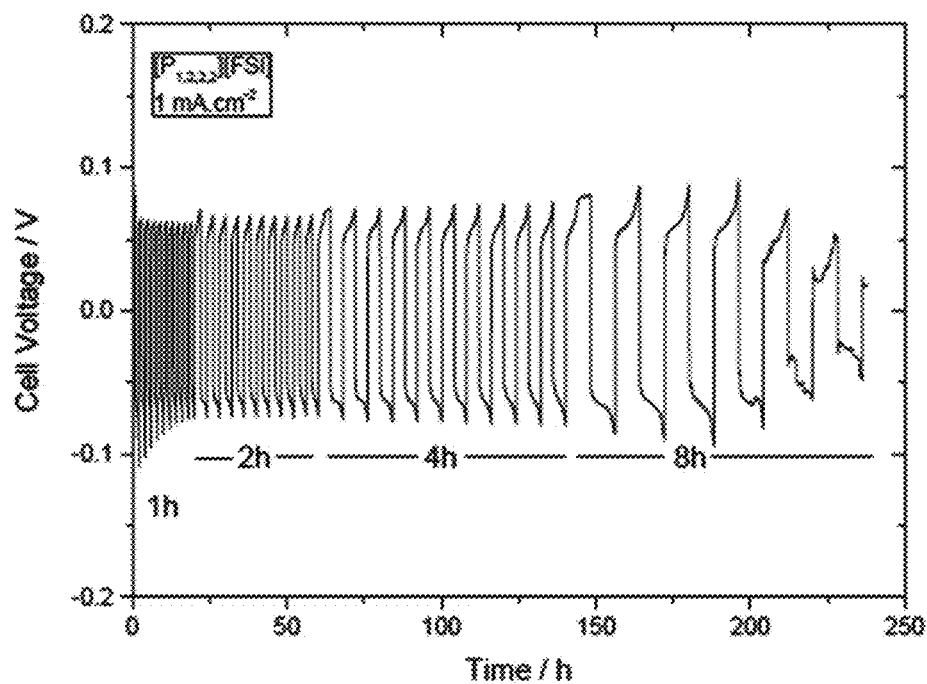
Figure 11C:
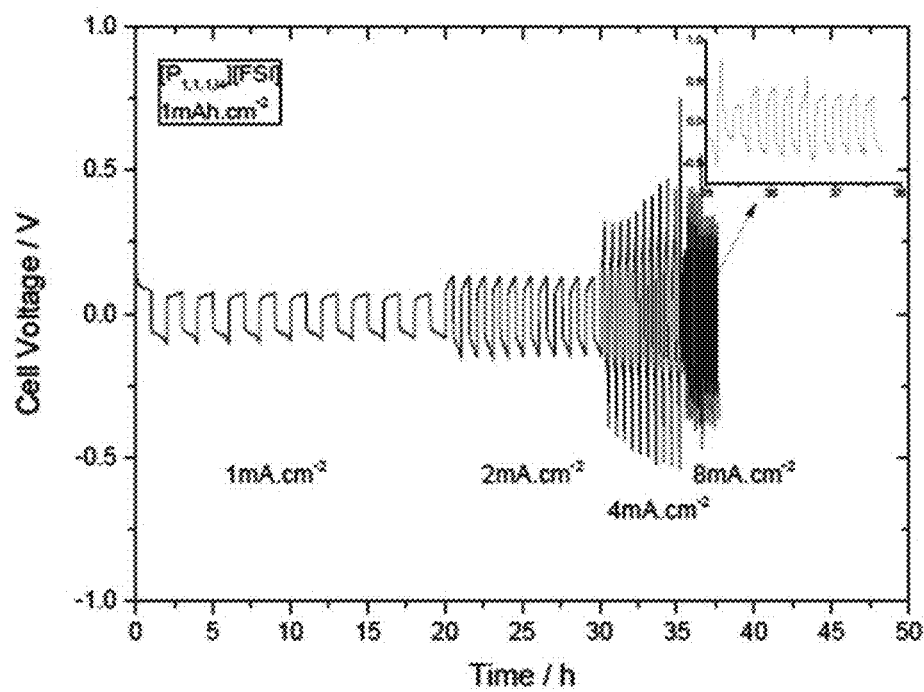
FIGS. 11C and 11D are plots of cell voltage vs. time for the cells of FIGS. 11A and 11B, having increasing current density while holding step capacity constant.
Figure 11D:
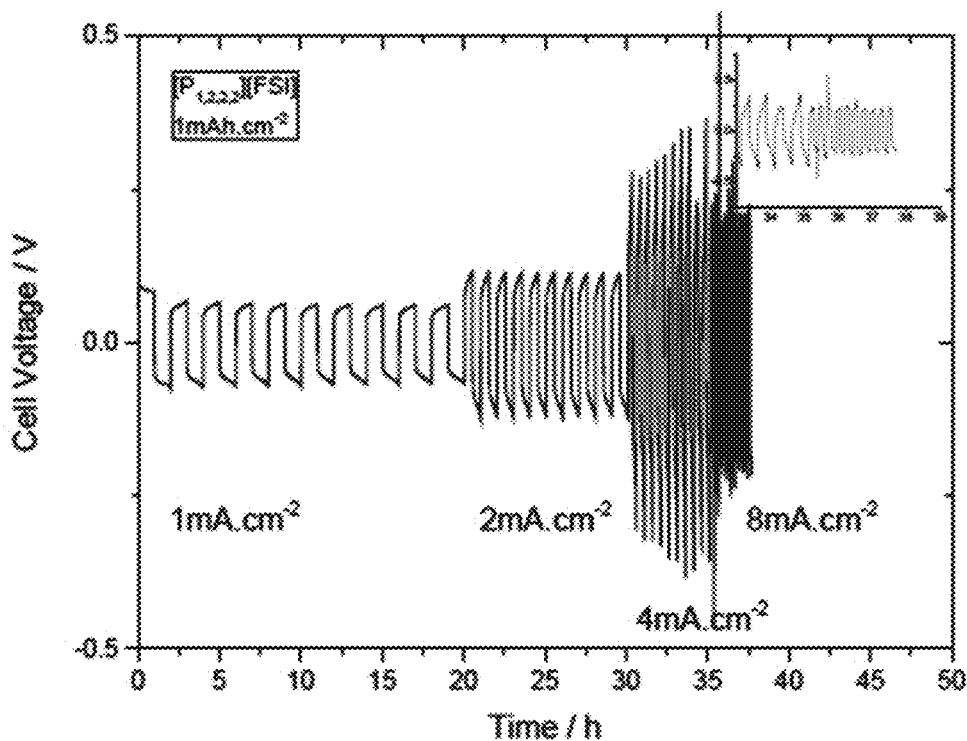

FIGS. 11A and 11B illustrate plots of cycling data for cells having $P_{1,1,1,i4}$:FSI ionic liquid or $P_{1,2,2,2}$:FSI ionic liquid, respectively, having increasing step times while holding current density constant. FIGS. 11C and 11D represent cycling data for the same cells, but with increasing current density while holding step capacity constant. Both electrolytes show similar performance limits, being able to sustain Li cycling up to 4 mAh·cm$^{-2}$ for 10 cycles when cycled at 1 mA·cm$^{-2}$, and 4 mA·cm$^{-2}$ when cycled at 1 mAh·cm$^{-2}$.

Figure 12:
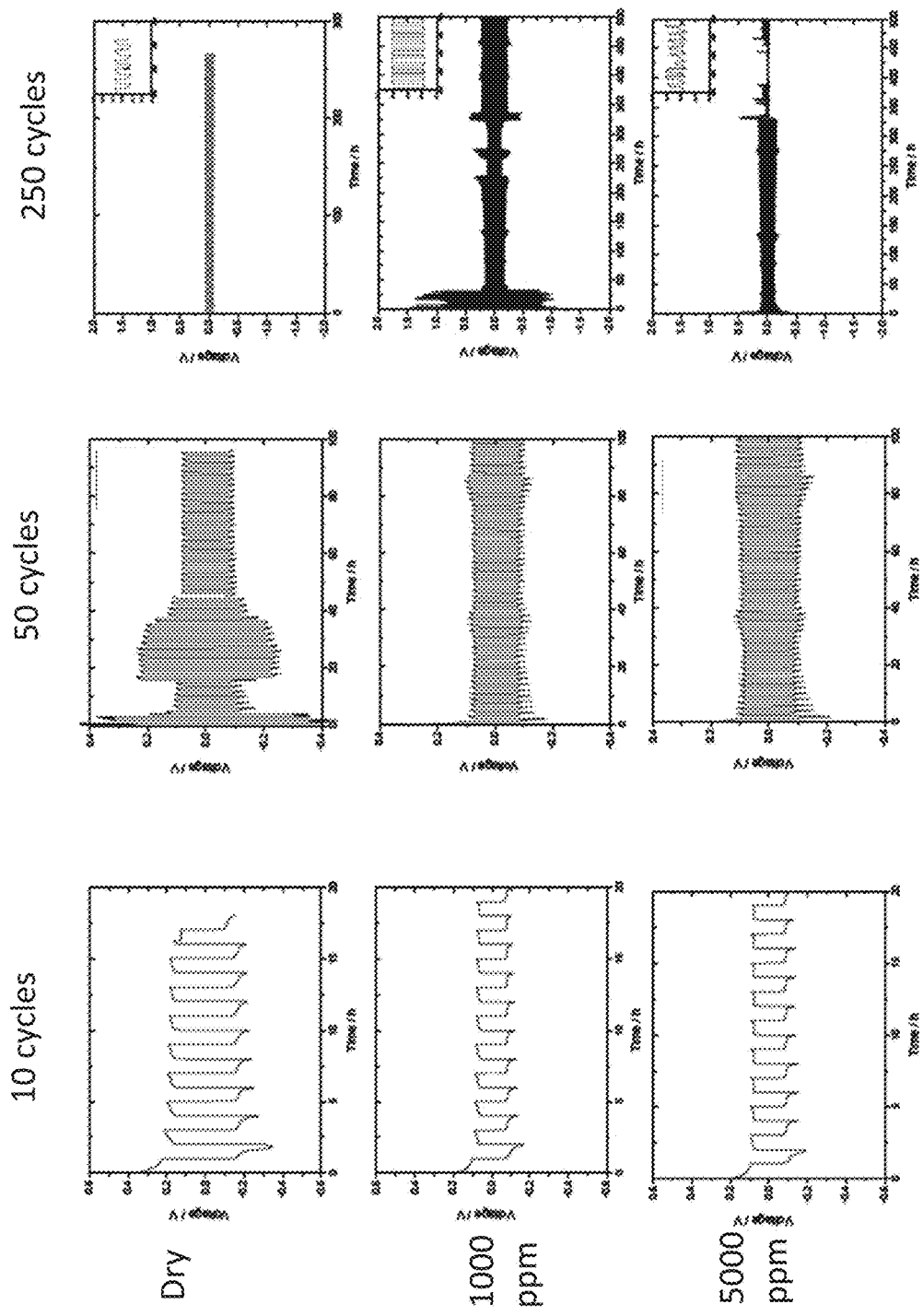
FIG. 12 is a panel of nine plots of cell voltage vs. time for cells having $P_{1,1,1,i4}$:FSI ionic liquid, for varying cycling durations and with varying water contents in the electrolyte.
Figure 13:
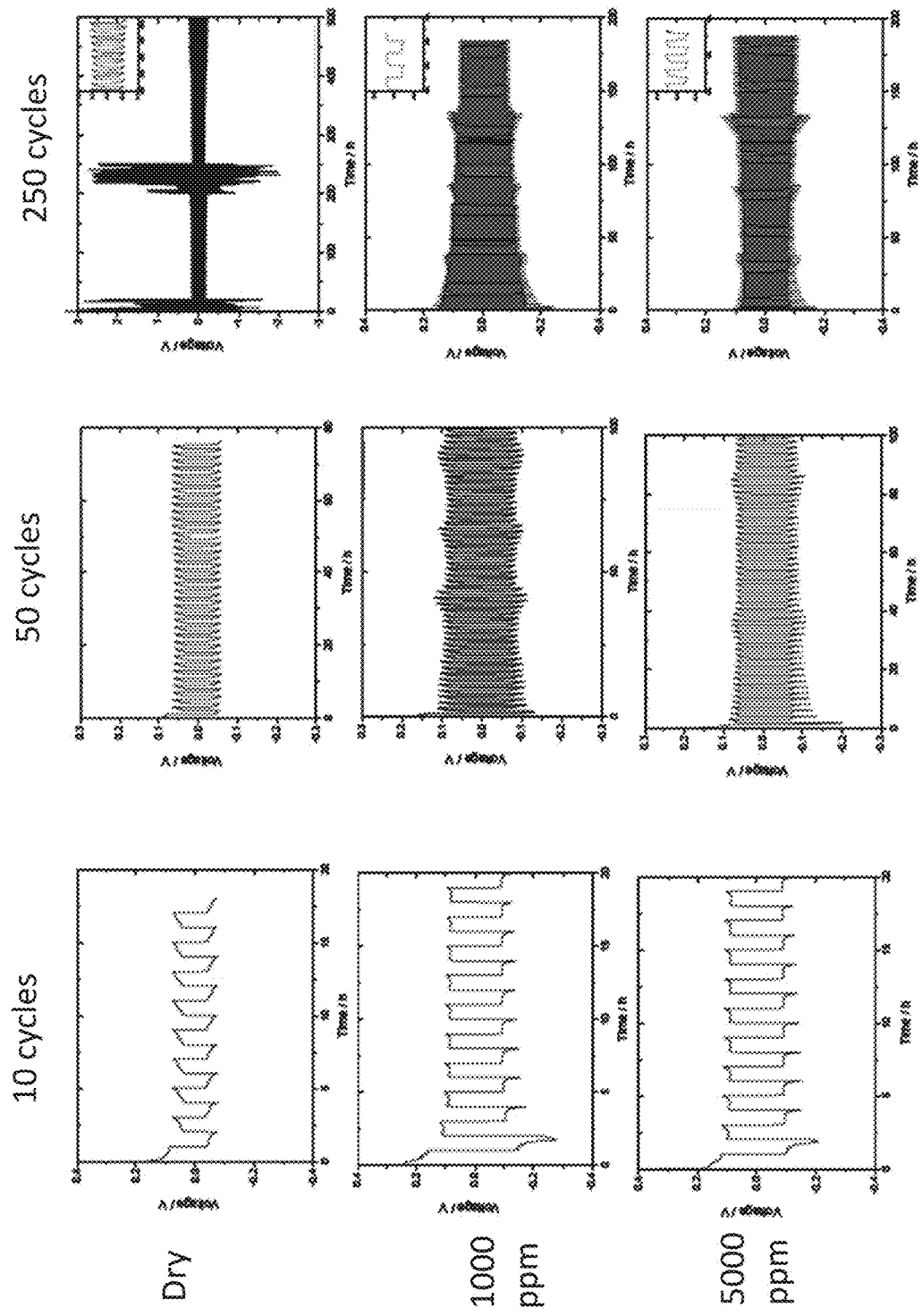
FIG. 13 is a panel of nine plots of cell voltage vs. time for cells having $P_{1,2,2,2}$:FSI ionic liquid, for varying cycling durations and with varying water contents in the electrolyte.

FIGS. 12 and 13 illustrate 9 plots each of cycling data for cells having $P_{1,1,1,i4}$:FSI ionic liquid or $P_{1,2,2,2}$:FSI ionic liquid, respectively, for varying cycling durations and with varying water contents in the electrolyte 130, and with phosphonium cation present at a 1:1 molar ratio relative to lithium cation. The cycling of lithium in both electrolytes in the absence of water shows good stability over 250 cycles. The initial overpotentials of both electrolytes are similar, sitting between 70-100 mV. There are some episodes of instability for the $P_{1,2,2,2}$-based ionic liquid during the initial and middle periods of the 250 cycle test, possibly artifactual. However, this does not appear to affect the long-term behavior of the cell after the episodes subside. The addition of 1000 ppm does appear to result in shorting in the $P_{1,1,1,i4}$ electrolyte after 225 h, with the cell shorting after 300 h of cycling in 5000 ppm. This suggests that the electrolyte having $P_{1,2,2,2}$:FSI ionic liquid may be the best performing among those disclosed herein.

The preceding description is merely illustrative in nature and is in no way intended to limit the disclosure, its application, or uses. As used herein, the phrase at least one of A, B, and C should be construed to mean a logical (A or B or C), using a non-exclusive logical "or." it should be understood that the various steps within a method may be executed in different order without altering the principles of the present disclosure. Disclosure of ranges includes disclosure of all ranges and subdivided ranges within the entire range.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment or particular system is included in at least one embodiment or aspect. The appearances of the phrase "in one aspect" (or variations thereof) are not necessarily referring to the same aspect or embodiment. It should be also understood that the various method steps discussed herein do not have to be carried out in the same order as depicted, and not each method step is required in each aspect or embodiment.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations should not be regarded as a departure from the disclosure, and all such modifications are intended to be included within the scope of the disclosure.

What is claimed is:

1. A secondary electrochemical cell comprising:
   an anode;
   a cathode; and
   an electrolyte comprising:
      a salt comprising an active metal cation, configured to be reduced at the anode during charging, and bis(fluorosulfonyl)imide (FSI);
      an ionic liquid comprising FSI and an organic cation selected from the group consisting of:
         methyltriethylphosphonium;
         trimethylisobutylphosphonium;
         methyltributylphosphonium; and
         trihexyltetradecylphosphonium; and
      water, present at a concentration of at least 50 ppm.

2. The cell as recited in claim 1, wherein the active metal cation comprises Li+.

3. The cell as recited in claim 2, wherein the anode comprises lithium metal.

4. The cell as recited in claim 1, wherein the salt is present, relative to the ionic liquid, at a molar ratio of at least 1:1.

5. The cell as recited in claim 1, wherein the salt is present at its saturation point in the ionic liquid.

6. The cell as recited in claim 1, wherein the organic cation comprises trimethylisobutylphosphonium.

7. The cell as recited in claim 1, wherein the organic cation comprises methyltriethylphosphonium.

8. The cell as recited in claim 1, wherein water is present at a concentration of at least 100 ppm.

9. The cell as recited in claim 1, wherein water is present at a concentration of at least 500 ppm.

10. The cell as recited in claim 1, wherein water is present at a concentration of at least 1000 ppm.

11. The cell as recited in claim 1, wherein water is present at a concentration of at least 4000 ppm.

12. An electrolyte composition comprising:
    a salt comprising an active metal cation and bis(fluorosulfonyl)imide (FSI);
    an ionic liquid comprising FSI and an organic cation selected from the group consisting of:
       methyltriethylphosphonium;

trimethylisobutylphosphonium;
methyltributylphosphonium; and
trihexyltetradecylphosphonium; and
water, present at a concentration of at least 50 ppm.

13. The electrolyte composition as recited in claim 12, wherein the active metal cation comprises Li+.

14. The electrolyte composition as recited in claim 12, wherein the organic cation comprises trimethylisobutylphosphonium.

15. The electrolyte composition as recited in claim 12, wherein the organic cation comprises methyltriethylphosphonium.

16. The electrolyte composition as recited in claim 12, wherein water is present at a concentration of at least 100 ppm.

17. The electrolyte composition as recited in claim 12, wherein water is present at a concentration of at least 500 ppm.

18. The electrolyte composition as recited in claim 12, wherein water is present at a concentration of at least 1000 ppm.

19. The electrolyte composition as recited in claim 12, wherein water is present at a concentration of at least 4000 ppm.

20. The electrolyte composition as recited in claim 12, wherein the salt is present at its saturation point in the ionic liquid.

* * * * *